United States Patent [19]
Gale et al.

[11] Patent Number: 5,512,292
[45] Date of Patent: *Apr. 30, 1996

[54] TRANSDERMAL CONTRACEPTIVE FORMULATIONS METHODS AND DEVICES

[75] Inventors: Robert M. Gale; Diane E. Nedberge, both of Los Altos; Linda E. Atkinson, Portola Valley, all of Calif.

[73] Assignee: ALZA Corporation, Palo Alto, Calif.

[ * ] Notice: the term of this patent shall not extend beyond the expiration date of Pat. No. 5,376,377.

[21] Appl. No.: 361,356

[22] Filed: Dec. 21, 1994

Related U.S. Application Data

[63] Continuation-in-part of Ser. No. 994,055, Dec. 17, 1992, Pat. No. 5,376,377, which is a continuation of Ser. No. 873,515, Apr. 20, 1992, abandoned, which is a continuation of Ser. No. 681,259, Apr. 8, 1991, abandoned, which is a continuation-in-part of Ser. No. 605,581, Oct. 29, 1990, abandoned.

[51] Int. Cl.$^6$ .................................................. A61F 13/02
[52] U.S. Cl. ........................ 424/448; 424/449; 514/843; 514/947
[58] Field of Search ................................. 424/448, 449; 514/843, 947

[56] References Cited

U.S. PATENT DOCUMENTS

| | | | |
|---|---|---|---|
| 3,598,122 | 8/1971 | Zaffaroni et al. | 128/268 |
| 3,598,123 | 8/1971 | Zaffaroni | 128/268 |
| 3,731,683 | 5/1973 | Zaffaroni | 128/268 |
| 3,797,494 | 3/1974 | Zaffaroni | 128/268 |
| 4,031,894 | 6/1977 | Urquhart et al. | 128/268 |
| 4,081,537 | 3/1978 | Hofmeister et al. | 424/238 |
| 4,201,211 | 5/1980 | Chandrasekaran et al. | 128/268 |
| 4,286,592 | 9/1981 | Chandrasekaran | 128/268 |
| 4,314,557 | 2/1982 | Chandrasekaran | 128/260 |
| 4,379,454 | 4/1983 | Campbell et al. | 604/897 |
| 4,435,180 | 3/1984 | Leeper | 604/896 |
| 4,559,222 | 12/1985 | Enscore et al. | 424/28 |
| 4,568,343 | 2/1986 | Leeper et al. | 604/896 |
| 4,573,995 | 3/1986 | Cheng et al. | 604/896 |
| 4,588,580 | 1/1989 | Gale et al. | 424/21 |
| 4,645,502 | 2/1987 | Gale et al. | 604/896 |
| 4,704,282 | 11/1987 | Campbell et al. | 424/424 |
| 4,746,515 | 5/1988 | Cheng et al. | 424/449 |
| 4,788,062 | 11/1988 | Gale et al. | 424/449 |
| 4,816,258 | 3/1989 | Nedberge et al. | 424/448 |
| 4,849,226 | 7/1989 | Gale | 424/448 |
| 4,863,738 | 9/1989 | Taskovich | 424/449 |
| 4,908,027 | 3/1990 | Enscore et al. | 604/890.1 |
| 4,943,435 | 7/1990 | Baker et al. | 424/448 |
| 5,004,610 | 4/1991 | Osborne et al. | 424/448 |

FOREIGN PATENT DOCUMENTS

| | | | |
|---|---|---|---|
| 532388 | 10/1988 | Australia | A61L 15/06 |
| 9004397 | 5/1990 | WIPO . | |

OTHER PUBLICATIONS

Knepp et al., "Transdermal Drug Delivery: Problems and Possibilities," CRC Critical Reviews in Therapeutic Drug Carrier System, vol. 4, Issue 1, pp. 13–37 (1987).

Pannatier, et al., "The Skin as a Drug Metabolizing Organ," Drug Metabolism Reviews, vol. 8, No. 2, pp. 319–343 (1978).

Primary Examiner—J. Gabrielle Phelan
Attorney, Agent, or Firm—Michael J. Rafa; Steven F. Stone; Edward L. Mandell

[57] ABSTRACT

The present invention provides compositions and methods for the transdermal administration of a contraceptively effective amount of gestodene and estrogen, such as ethinyl estradiol, in combination, together with a suitable permeation enhancer. The amount of the estrogen codelivered is kept at an about constant and contraceptively effective rate while the amount of gestogen codelivered varies depending on the phase of the menstrual cycle but remains at a contraceptively effective rate. The size of the system may also vary depending on the amount of gestogeno be delivered.

31 Claims, 2 Drawing Sheets

FIG. 4

TRANSDERMAL CONTRACEPTIVE FORMULATIONS METHODS AND DEVICES

RELATED APPLICATIONS

This is a continuation-in-part of U.S. application Ser. No. 07/994,055, filed Dec. 17, 1992, now U.S. Pat. No. 5,376, 377, which was a continuation application of U.S. application Ser. No. 07/873,515, filed Apr. 20, 1992, now abandoned, which was a continuation application of U.S. Ser. No. 7/681,259, filed Apr. 8, 1991, now abandoned, which was a continuation-in-part of U.S. application Ser. No. 07/605, 581, filed Oct. 29, 1990 now abandoned, which applications are incorporated herein in their entirety by reference and benefit is claimed of their filing dates.

FIELD OF THE INVENTION

This invention relates to transdermal drug delivery. More particularly, this invention relates to transdermal drug delivery to provide a contraceptive effect, and, still more particularly but without limitation thereto, this invention relates to the transdermal delivery of gestodene and estrogens, such as ethinyl estradiol, in combination, each at contraceptively effective rates. In one embodiment of this invention, the amount of ethinyl estradiol delivered is maintained at about a constant level, while the amount of gestodene delivered varies depending on the phase of a woman's menstrual cycle. Optionally, the size of the transdermal device varies depending on the amount of gestodene desired to be delivered.

BACKGROUND OF THE INVENTION

The transdermal route of parenteral delivery of drugs provides many advantages, and transdermal systems for delivering a wide variety of drugs or other beneficial agents are described in U.S. Pat. Nos. 3,598,122; 3,598,123; 3,731, 683; 3,797,494; 4,031,894; 4,201,211; 4,286,592; 4,314, 557; 4,379,454; 4,435,180; 4,559,222; 4,568,343; 4,573, 995; 4,588,580; 4,645,502; 4,704,282; 4,788,062; 4,816, 258; 4,849,226; 4,908,027; 4,943,435; and 5,004,610, all of which are incorporated herein by reference.

Gestodene is a known orally active synthetic progestogen with a progesterone-like profile of activity. See, U.S. Pat. No. 4,081,537 incorporated herein in its entirety by reference. It is used as an oral contraceptive in combination with certain estrogens.

Oral combination pills and intrauterine devices for purposes of contraception have been well documented for their problems such as inconvenience and side effects. Transdermal delivery of contraceptives as disclosed herein is an attempt to eliminate or reduce those problems.

There are many factors, however, which affect the suitability of an active agent for transdermal administration. These are discussed at length in Knepp et al, "Transdermal Drug Delivery: Problems and Possibilities," CRC Critical Reviews in Therapeutic Drug Carrier Systems, Vol. 4, Issue 1 (1987). When it is desired to deliver more than one active agent from a single transdermal delivery device, the problems associated with achieving a workable multi-drug transdermal device with any specific combination of drugs are even more complex and difficult and can often prove to be insurmountable.

Conventional dosage forms such as tablets or injections can administer a combination of two or more active agents, each at their appropriate dose, merely by appropriate selection of the amount of each agent included in the dosage form. In transdermal delivery devices, however, the total dosage of each agent is not established by the amount of each agent that is in the device. Instead, the total dosage of each agent is the product of its average transdermal administration rate (μg/hr) and the time over which the device is applied, and the average administration rate of an agent from a transdermal delivery device is determined primarily by a combination of factors other than the amount of the agent present in the device.

In order for a transdermal delivery device to be able to administer two or more agents from a common reservoir over the same period of time, the relative permeabilities of each of the agents through the skin and the components of the device must bear the same relationship as their relative dosage or administration rate. Thus, for example, if the dosage of each agent were the same, for example 15 μg/day, each agent would have to have the same overall permeability. If, however, one agent were to be delivered at a dosage of 20 μg/day and the other at 1 μg/day, the overall permeability of one would have to be 20 times greater than that of the other.

The situation becomes even more complicated if permeation enhancers are required to increase the inherent permeability of the skin to one or more of the agents being delivered. Identifying a permeation enhancer that has the ability to selectively increase the permeation of the skin to only one agent or to relatively increase the permeability of the skin to two or more agents in the required relationship could often provide an insurmountable obstacle for any specific combination of agents.

If the problems associated with obtaining the desired relative administration rates of the individual agents to the skin can be solved, other factors remain with which to be dealt. The agents individually, in combination with each other, or in combination with a permeation enhancer, must not cause undue irritation or sensitization when applied topically under occlusion. Materials which individually are not irritating or sensitizing may become so when presented to the skin in combination with each other.

Further, the skin has been recognized as the largest metabolizing organ of the body, larger even than the liver. See, A. Pannatier, et al, "The Skin as a Drug Metabolizing Organ," Drug Metabolism Reviews, Vol. 8, No. 2, pp 319–343(1978). Skin can metabolize agents administered transdermally into inactive or potentially harmful metabolites. Thus, it is necessary that the rate at which each agent is metabolized by the skin and the metabolites produced do not prevent the safe and therapeutically effective transdermal administration of each agent into the bloodstream at the desired administration rate.

Assuming these obstacles can be overcome, it is also important that the agent binding capacity of the skin for each of the agents have the proper relationship. Before transdermal administration of an agent into the bloodstream can commence at a steady state rate, the capacity of the skin below the device to bind the agent must be saturated. The time required to achieve this steady state rate is known as the "lag time" and is a function of the rate at which the agent permeates into the skin and the binding capacity of the skin for that agent. In order for the lag time for both agents to be the same, there must be an inverse relationship between each agent's administration rate and the binding capacity of the skin for each agent.

Thus, while there are numerous combinations of beneficial agents which have been found useful for administration orally or by injection, for example, it is by no means obvious that a particular combination of such agents or other agents could also be safely and effectively administered transdermally.

Another obstacle to be considered is the complexity of a woman's menstrual cycle. The menstrual cycle is the result of a complex feedback system including the sex hormones estrogen and progesterone, the pituitary gonadotropins LH and FSH, and gonadotropin-releasing hormones (GnRH) from the hypothalamus. Estrogen in low concentrations inhibits the production of FSH and GnRH (and so of LH). In high concentrations, estrogen stimulates the production of LH and GnRH (and so of FSH). Estrogen and progesterone together inhibit the production of GnRH.

At the beginning of the menstrual cycle, hormone levels are low, e.g., progesterone is virtually absent and estrogen is low but rising. After the menstrual flow ceases and under the influence of the gonadotropin hormones FSH and LH, an egg cell and its follicle begin to mature. The follicle, as it enlarges, secretes increased amounts of estrogen. The rapid rise in estrogen levels near the midpoint of the cycle triggers a sharp increase in production of LH by the pituitary gland that stimulates the follicle to release the egg cell. Thus, the second week is typified by rapidly increasing estrogen, ovulation and moderate amounts of progestin.

Under the continued stimulus of LH, the cells of the emptied follicle grow producing the corpus luteum, which begin to synthesize significant amounts of progesterone, as well as estrogens. Thus, the third week is typified by the highest amounts of progesterone and moderate estrogens. As the progesterone levels increase, estrogen and progesterone together inhibit the production of GnRH, and of gonadotropin hormones, LH and FSH, from the pituitary. As a result of this drop in the level of gonadotropic hormones, production of ovarian hormones drops. Thus, the fourth week of the cycle is typified by declining estrogens and progesterone, with menses ensuing and the monthly cycle begins again.

A contraceptive cycle of estrogen and progestin can mimic the hormone pattern described above. However, the reproductive tract and other estrogen sensitive organs (skin, bone, vascular, etc.) require low to moderate estrogens, e.g., above the post-menopausal level, but not in the excess found in the menstrual cycle during the phase of follicular growth and ovulation activities. Contraceptively effective hormone therapy is designed to keep the level of ovarian hormones in the blood high enough to shut off production of the pituitary hormones FSH and LH so that ovarian follicles do not open and no ovulation occurs, but lower than the excess levels described above.

U.S. Pat. No. 4,816,258 incorporated herein in its entirety by reference discloses a transdermal delivery system for administering ethinyl estradiol and levonorgestrel, together with a permeation enhancer, as a contraceptive. It has now been found by the present inventors that levonorgestrel, even in the presence of a permeation enhancer such as glycerol monooleate, does not sufficiently transport across human epidermis in vivo to achieve therapeutically (ie, contraceptively) effective levels of the drug in the blood from transdermal systems of reasonable or acceptable size.

Surprisingly, it has now been seen that gestodene, while being approximately equipotent with levonorgestrel when applied orally, acts very differently from levonorgestrel when applied transdermally. Gestodene, unpredictably, has a greatly increased flux in comparison to levonorgestrel. The flux of gestodene is sufficient when applied transdermally to provide blood drug levels in amounts that produce effective contraception at each of the different phases of the menstrual cycle, in marked contrast to levonorgestrel.

Australian Patent No. AU-A-15323/88, incorporated herein in its entirety by reference, discloses a transdermal delivery system for the delivery of estrogens and synthetic gestogens for the treatment of climacteric syndrome (the withdrawal symptoms associated with menopause and caused by estrogen deficiency). The patent makes a general statement that natural gestogens, such as progesterone, do not pass through the skin in amounts sufficient to achieve adequate therapeutic effect using transdermal systems of conventional size but that synthetic gestogens do have sufficient flux. Levonorgestrel (or d-norgestrel) is named in the patent as a synthetic gestogen which can be used in the transdermal system, and norgestrel and norethisterone-17-acetate are named as preferred synthetic gestogens for use in the system. Gestodene is not mentioned as a candidate gestogen. It is to be noted here that a markedly greater amount of a gestogen and, consequently, a greater transdermal flux of the drug, is required for effective contraception than is required for treatment of climacteric syndrome. As discussed previously herein, it has been shown that levonorgestrel, the active enantiomer of the preferred gestogen norgestrel, does not, in fact, have a sufficient flux to provide a contraceptively effective amount of drug in vivo when applied transdermally from a reasonably sized system. Additionally, norethisterone-17-acetate (also known as norethindrone-17-acetate and the only drug for which actual data is presented in the Australian patent) has also been found to have an insufficient transdermal flux from a reasonably sized system to provide sufficient blood levels for effective contraception. These facts show that the broad statement in the Australian patent is not generally true and that sufficient flux of synthetic gestogens, particularly with respect to providing a contraceptive effect, is a continuing problem and cannot be predicted.

U.S. Pat. No. 4,286,592, incorporated herein in its entirety by reference, discloses a transdermal system with a contact adhesive layer, where the adhesive layer controls the rate at which drug is released to the skin.

U.S. Pat. No. 4,379,454, incorporated herein in its entirety by reference, discloses a transdermal system which includes a rate controlling layer for controlling the rate at which an absorption enhancer is released to the skin.

U.S. Pat. No. 4,863,738, incorporated herein in its entirety by reference, discloses glycerol monooleate as a suitable skin permeation enhancer for steroids.

U.S. Pat. No. 4,746,515, incorporated herein in its entirety by reference, discloses glycerol monolaurate as a suitable skin permeation enhancer for steroids.

SUMMARY OF THE INVENTION

Thus, it is by no means obvious that a particular synthetic gestogen could be effectively coadministered transdermally, with an estrogen, and especially in an amount sufficient to provide a contraceptive effect. The amount of gestogen codelivered would vary depending on the phase of the menstrual cycle, while the amount of estrogen codelivered would remain about constant throughout the menstrual cycle. Optionally, the system size would vary depending on the amount of gestodene required to be codelivered. That the gestogen could be codelivered in a varying but contraceptively effective amount while the amount of estrogen codelivered remains about constant, is especially desired and even less predictable or obvious. Further that both the estrogen and gestogen are codelivered in a contraceptively effective amount from a variety of system sizes is by no means obvious.

An aspect of the present invention is to provide delivery of contraceptives by means of transdermal devices.

A further aspect of the invention is to coadminister estrogens and gestodene transdermally at contraceptively effective rates.

Another aspect of the invention is to provide a method for the transdermal coadministration of estrogens and gestodene, at contraceptively effective rates wherein the amount of estrogen codelivered is kept about constant throughout the menstrual cycle while the amount of gestodene codelivered varies throughout the menstrual cycle.

Yet another aspect of the invention is to coadminister estrogens at a constant contraceptively effective rate throughout the menstrual cycle and gestodene at a varying but contraceptively effective rate from transdermal systems of different sizes depending on the amount of gestodene to be delivered.

Still another aspect of the invention is to provide a kit for obtaining contraception on a 28-day interval comprising transdermal devices for delivering a constant contraceptively effective rate of an estrogen and a varying rate of gestodene.

The aspects mentioned above, as well as others, have been demonstrated by the present invention, which provides a device and method for the transdermal coadministration of a contraceptively effective amount of gestodene and an estrogen, such as ethinyl estradiol, together with a skin permeation-enhancing amount of a suitable permeation enhancer. The drugs are coadministered from reasonably sized systems which may vary in size that depending on the amount of gestodene to be delivered, which is in turn dependent on the phase of a woman's menstrual cycle. The level of estrogen codelivered is kept about constant regardless of the system size.

The systems of the invention are transdermal drug delivery devices comprising a matrix adapted to be placed in drug- and permeation enhancer-transmitting relation with the skin site. The matrix contains sufficient amounts of a permeation enhancer and, of an estrogen and gestodene, in combination, to continuously coadminister to the skin, for a predetermined period of time, the drugs and the permeation enhancer to provide effective contraception. The amount of estrogen codelivered will remain about constant, while the amount of gestodene codelivered from the systems will vary depending on the phase of the menstrual cycle of the woman wearing the system. Optionally, the size of the device may vary depending on the amount of gestodene codelivered. The size of the device is selected from a variety of reasonable sizes useful for the application of the drugs and the enhancer to a human body. By "reasonable size", as used herein, is meant a device of a size with a base surface area (that area in contact with the skin site) that is between 1 cm$^2$ to 50 cm$^2$, preferably about 3.5 cm$^2$, about 7.0 cm$^2$, or about 14 cm$^2$.

The systems of the invention can be designed to codeliver the estrogen and gestogen for an extended time period, e.g., up to seven days. By designing systems that codeliver varying amounts of gestogen, one can construct a kit for a 28-day contraceptive cycle. The kit would contain (1) three seven-day systems of the present invention, e.g., three systems that codeliver gestogen and estrogen and (2) a fourth seven-day system delivering either low or no estrogen and no gestogen.

A woman would use the kit of the present invention according to the following procedure: (1) during the seven days during and after menstruation, she would wear the system delivering no gestogen and little or no estrogen e.g., about 50 μg/day estradiol or about 10–20 μg/day ethinyl estradiol; (2) during the second week she would wear a system codelivering a low but contraceptively effective amount of gestogen and contraceptively effective amount of estrogen, which will remain constant during the remainder of the 28-day cycle, e.g., 25 μg/day gestodene and 20–50 μg/day ethinyl estradiol; (3) during the third week, she would wear a system codelivering a high and contraceptively affective amount of gestogen and a contraceptively effective amount of estrogen, e.g., 100 μg/day gestodene and 30–50 μg/day ethinyl estradiol; and (4) during the fourth week she would wear a system codelivering a medium but contraceptively effective amount of gestogen and a contraceptively effective amount of estrogen, e.g., 50 μg/day gestodene and 30–50 μg/day ethinyl estradiol.

DETAILED DESCRIPTION OF THE INVENTION

This invention utilizes principles of transdermal drug delivery to provide a novel system for effectively administering contraceptives to a woman throughout her menstrual cycle. The varying hormone requirements are met by altering the amount of gestogen delivered. Optionally, the sizes of transdermal delivery devices may be altered as well. More particularly, the present invention provides continuous coadministration of an estrogen, such as ethinyl estradiol, and gestodene through the skin or mucosa for up to seven days or longer, from a variety of reasonably sized systems. A suitable permeation enhancer is present together with the drugs. The fluxes of the drug formulations provided by this invention are sufficient to achieve contraceptively effective levels of the estrogen and the gestodene from transdermal systems of reasonable size while maintaining a constant level of delivered estrogen (as needed for contraception) regardless of the size of the system. The amount of gestogen delivered varies depending on the changing hormonal requirements of a woman during her menstrual cycle.

Figure 1:
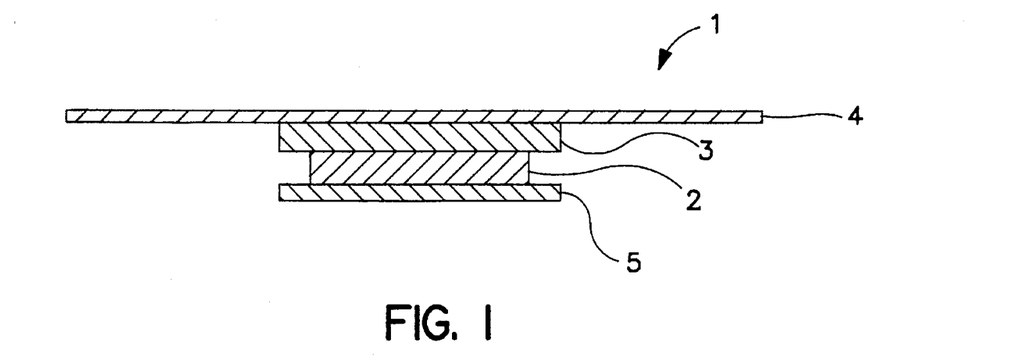
FIG. 1 is a cross-sectional view of one embodiment of a transdermal therapeutic drug delivery device which may be used in accordance with the present invention.
Figure 3:
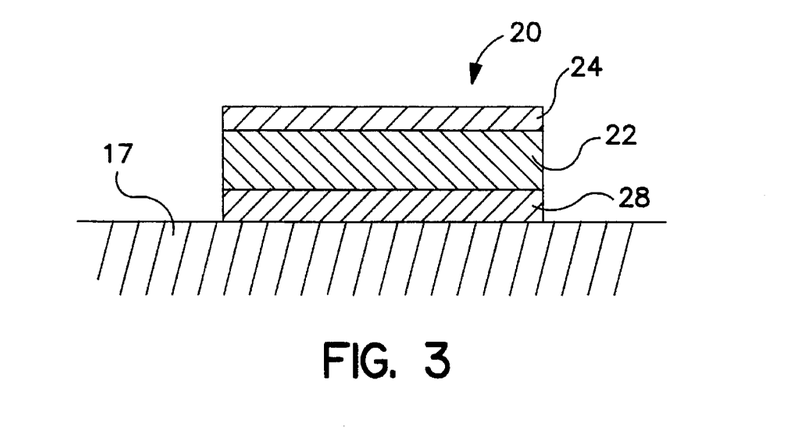
FIG. 3 is a cross-sectional view of yet another embodiment of a transdermal therapeutic drug delivery device which may be used in accordance with this invention.

One embodiment of a transdermal delivery device of the present invention is illustrated in FIG. 1. In FIG. 1, device 1 is comprised of a gestodene-, estrogen- and permeation enhancer-containing reservoir ("drug reservoir") 2, which is preferably in the form of a matrix containing the drugs and the enhancer dispersed therein. An impermeable backing layer 3 is provided adjacent to one surface of drug reservoir 2. An adhesive overlay 4 maintains the device 1 on the skin and may be fabricated together with, or provided separately from, the remaining elements of the device. With certain formulations, the adhesive overlay 4 may be preferable to an in-line contact adhesive, such as adhesive layer 28 as shown in FIG. 3. This is true, for example, where the drug reservoir contains a material (such as, for example, an oily surfactant permeation enhancer) which adversely affects the adhesive properties of the in-line contact adhesive layer 28. Impermeable backing layer 3 is preferably slightly larger than drug reservoir 2, and in this manner prevents the materials in drug reservoir 2 from adversely interacting with the adhesive in overlay 4. A strippable or removable liner 5 is also provided with device 1 and is removed just prior to application of device 1 to the skin.

Figure 2:
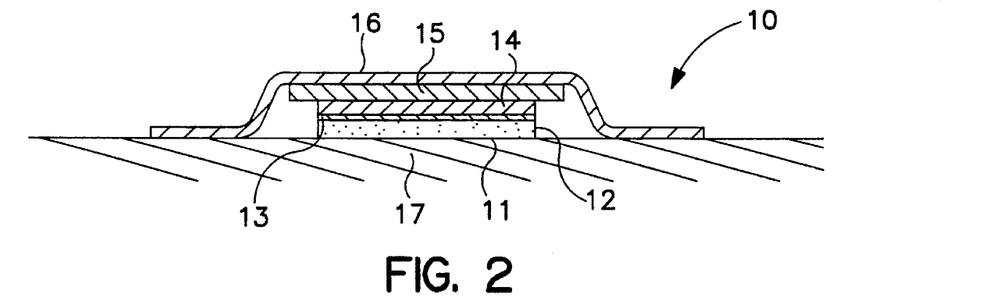
FIG. 2 is a cross-sectional view of another embodiment of a transdermal therapeutic drug delivery device which may be used in accordance with the present invention.

FIG. 2 illustrates another embodiment of the invention, device 10, shown in place upon the skin 17. In this embodiment, the transdermal therapeutic delivery device 10 comprises a multilaminate drug formulation/enhancer reservoir 11 having at least two zones 12 and 14. Zone 12 consists of a drug reservoir substantially as described with respect to FIG. 1. Zone 14 comprises a permeation enhancer reservoir which is preferably made from substantially the same matrix as is used to form zone 12. Zone 14 comprises a permeation enhancer dispersed throughout and may contain estrogen and/or gestodene at or below saturation when at equilibrium. A rate-controlling membrane 13 for controlling the release rate of the enhancer from zone 14 to zone 12 is placed between the two zones. A rate-controlling membrane (not shown) for controlling the release rate of the enhancer from zone 12 to the skin may also optionally be utilized and would be present between the skin 17 and zone 12.

The rate-controlling membrane may be fabricated from permeable, semipermeable or microporous materials which are known in the art to control the rate of agents into and out of delivery devices and having a permeability to the permeation enhancer lower than that of zone 12. Suitable materials include, but are not limited to, polyethylene, polyvinyl acetate and ethylene vinyl acetate copolymers.

An advantage of the device described in FIG. 2 is that the drug-loaded zone 12 is concentrated at the skin surface rather than throughout the entire mass of the reservoir 11. This functions to reduce the amount of drugs in the device while maintaining an adequate permeation enhancer supply.

Superimposed over the drug formulation/enhancer reservoir 11 of device 10 is an impermeable backing 15 and an adhesive overlay 16 as described above with respect to FIG. 1. In addition, a strippable liner (not shown) would preferably be provided on the device prior to use as described with respect to FIG. 1 and removed prior to application of the device 10 to the skin 17.

In the embodiments of FIGS. 1 and 2, the carrier or matrix material has sufficient viscosity to maintain its shape without oozing or flowing. If, however, the matrix or carrier is a low viscosity flowable material, the composition can be fully enclosed in a pouch or pocket formed between the impermeable backing and a permeable or microporous skin-contacting membrane, as known to the art from U.S. Pat. No. 4,379,454 (noted above), for example.

An example of a presently preferred transdermal delivery device is illustrated in FIG. 3. In FIG. 3, transdermal delivery device 20 comprises a drug reservoir 22 containing the gestodene, the estrogen and the permeation enhancer. Reservoir 22 is preferably in the form of a matrix containing the drugs and the enhancer dispersed therein. Reservoir 22 is sandwiched between a backing layer 24, which is impermeable to both the drugs and the enhancer, and an in-line contact adhesive layer 28. In FIG. 3, the drug reservoir 22 is formed of a material, such as a rubbery polymer, that is sufficiently viscous to maintain its shape. The device 20 adheres to the surface of the skin 17 by means of the contact adhesive layer 28. The adhesive for layer 28 should be chosen so that it is compatible and does not interact with any of the estrogen or gestodene or, in particular, the permeation enhancer. The adhesive layer 28 may optionally contain enhancer and/or drugs. A strippable liner (not shown) is normally provided along the exposed surface of adhesive layer 28 and is removed prior to application of device 20 to the skin 17. In an alternative embodiment, a rate-controlling membrane (not shown) is present and the drug reservoir 22 is sandwiched between backing layer 24 and the rate-controlling membrane, with adhesive layer 28 present on the skin-side of the rate-controlling membrane.

Various materials suited for the fabrication of the various layers of the transdermal devices of FIGS. 1, 2 or 3 are known in the art or are disclosed in the aforementioned transdermal device patents previously incorporated herein by reference.

The matrix making up the gestodene/estrogen/permeation enhancer reservoir can be a gel or a polymer. Suitable materials should be compatible with gestodene, the estrogen, the permeation enhancer and any other components in the system. Suitable matrix materials include, without limitation, natural and synthetic rubbers or other polymeric material, thickened mineral oil, or petroleum jelly, for example. The matrix is preferably polymeric and is more preferably an anhydrous polymer. A preferred embodiment according to this invention is fabricated from an ethylene vinyl acetate (EVA) copolymer, of the type described in U.S. Pat. No. 4,144,317, and is preferably selected from those EVAs having a vinyl acetate (VA) content in the range of about 9 to 60%, preferably about 28 to 60% VA. Particularly good results may be obtained using EVA of 40% vinyl acetate content.

In addition to gestodene, an estrogen and a permeation enhancer, which are essential to the invention, the matrix may also contain stabilizers, dyes, pigments, inert fillers, tackifiers, excipients and other conventional components of transdermal delivery devices as are known in the art.

The amounts of the estrogen and of gestodene that are present in the therapeutic device, and that are required to achieve a contraceptive effect, depend on many factors, such as the minimum necessary dosage of each drug; the permeability of the matrix, of the adhesive layer and of the rate-controlling membrane, if present; and the period of time for which the device will be fixed to the skin. Because the drugs are to be released over a period of more than one day, there is, in fact, no upper limit to the maximum amounts of the drugs present in the device. The minimum amount of each drug is determined by the requirement that sufficient quantities of drug must be present in the device to maintain the desired rate of release over the given period of application.

The gestodene is generally dispersed through the matrix at a concentration in excess of saturation, i.e. at unit activity. The amount of excess is determined by the intended useful life of the system. When the estrogen is the natural estrogen 17β-estradiol, it is also generally present in the matrix at a concentration in excess of saturation. The concentration of a synthetic estrogen, such as ethinyl estradiol, in the matrix is generally in an amount below saturation, because the flux of the estrogen through human epidermis has been found to be proportional to the concentration of estrogen in the drug reservoir. The dosage for the estrogen, ethinyl estradiol, should not exceed 50 µg/day because of safety concerns. The permeation enhancer is dispersed through the matrix, preferably at a concentration sufficient to provide permeation-enhancing concentrations of enhancer in the reservoir throughout the anticipated administration period.

The permeation enhancer useful in the present invention is selected from those compounds which are compatible with gestodene and with the estrogen and which provide enhanced skin permeation to these two drugs when it is administered together with the drugs to the skin of a user. Additionally, the permeation enhancer must not adversely interact with the adhesive of the in-line contact adhesive layer. Such permeation enhancers can be selected from, but are not limited to, $C_{2-4}$ alcohols such as ethanol and isopropanol, polyethylene glycol monolaurate, dimethyl lauramide, esters of fatty acids having from about 10 to about 20 carbon atoms, and monoglycerides or mixtures of monoglycerides of fatty acids.

Typically, monoglycerides have been available as a mixture of monoglycerides of fatty acids with one monoglyceride being the principal component, from which component the mixture derives its name. For example, one commercial monoglyceride is Emerest 2421 glycerol monooleate (Emery Division, Quantum Chemical Corp.), which is a mixture of glycerol oleates with a glycerol monooleate content of 58% and a total monoesters content of 58%. Other examples of commercial monoglycerides are Myverol 1899K glycerol monooleate (Eastman Chemical Products) which has a glycerol monooleate content of 61% and a total monoesters content of 93%, and Myverol 1892K glycerol monolinoleate which has a glycerol monolinoleate content of 68% and a minimum total monoesters content of 90%. The monoesters are chosen from those with from 10 to 20 carbon atoms. The fatty acids may be saturated or unsaturated and include, for example, lauric acid, myristic acid, stearic acid, oleic acid, linoleic acid and palmitic acid. Monoglyceride permeation enhancers include glycerol monooleate, glycerol monolaurate and glycerol monolinoleate, for example. In a presently preferred embodiment of this invention, the permeation enhancer is a monoglyceride or a mixture of monoglycerides of unsaturated fatty acids, and more preferred is glycerol monooleate (GMO) or glycerol monolinoleate. As used herein and in the appended claims, the term "monoglyceride" refers to a monoglyceride or a mixture of monoglycerides of fatty acids.

It has been seen that glycerol monooleate having a total monoesters content of less than about 65% interacts adversely with known adhesive materials to such an extent that the adhesive cannot function to maintain a delivery device on the skin. Therefore, when an in-line adhesive is present as a part of the device of the invention so that a permeation enhancer must pass through the adhesive, and when glycerol monooleate is utilized as the permeation enhancer, the glycerol monooleate must have a total monoesters content of at least 65%.

The contraceptive system of the invention contains a drug formulation comprising an estrogen and gestodene, the amount of estrogen delivered is constant regardless of the system size. The amount of gestodene delivered varies depending on the different phases of the woman's menstrual cycle. The size of the transdermal system may change based upon the amount of gestodene to be delivered. One embodiment of the invention is directed to systems having a relatively small surface area about 3.5 cm² that are designed to codeliver 25 µg/day of gestodene and 20–50 µg/day of estrogen for the first week of application per cycle beginning after menses. Another embodiment of the invention is directed to systems having a relatively medium surface area e.g., about 7 cm² that are designed to codeliver 50 µg/day of gestodene and 30–50 pg/day of estrogen for the third week of application per cycle. Yet another embodiment of the invention is directed to systems having a relatively larger surface area, e.g., about 14 cm² designed to codeliver 100 µg/day of gestodene and 30–50 µg/day estrogen for the second week of application per cycle. The overall contraception system of the invention also includes transdermal system designed to deliver low estrogen, e.g., 50 µg/day estradiol or 10 µg/day ethinyl estradiol and no gestodene for the week of menses per cycle. Alternatively, this system may be a placebo.

The term "estrogen" includes both the natural 17β-estradiol and estrone and the semi-synthetic estrogen derivatives such as the esters of natural estrogen, such as estradiol-17β-enanthate, estradiol- 17β-valerate, estradiol-3-benzoate, estradiol-17β-undecenoate, estradiol-16,17-hemisuccinate or estradiol-17β-cypionate; 17-alkylated estrogens, such as ethinyl estradiol, ethinyl estradiol-3-isopropylsulphonate, quinestrol, mestranol or methyl estradiol; estrone and non-steroidal compounds having estrogen activity, such as diethylstilbestrol, dienestrol, clomifen, chlorotrianisen or cyclofenil. The drug formulation of the invention preferably contains 17β-estradiol or ethinyl estradiol as the estrogen.

In the present invention, gestodene and an estrogen, such as ethinyl estradiol, are codelivered, in combination, at a contraceptively effective rate (that is, a rate that provides effective contraception) and the permeation enhancer is delivered at a permeation-enhancing rate (that is, a rate that provides increased permeability of the application site to both the estrogen and gestodene) for a predetermined time period.

The required transdermal flux of estrogen for effective contraception as provided by systems of this invention i.e., those involving the codelivery of gestogen and estrogen, is to remain constant at about 30 µg/day and not to exceed about 50 µg/day of ethinyl estradiol, regardless of the size of the system. The transdermal flux of gestodene according to embodiments of this invention, i.e., those that provide codelivery of gestodene and estrogen, ranges from about 25 µg/day to about 100 µg/day. The placebo or low estrogen system delivers no gestogen.

The devices of this invention can be designed to effectively deliver an estrogen and gestodene for an extended time period of up to 7 days or longer. Seven days is generally the maximum time limit for application of a single device because the skin site is adversely affected by a period of occlusion greater than 7 days. The drug delivery must be continuous in order to provide effective contraception. Therefore, when one device has been in place on the skin for its effective time period, it is replaced with a fresh device, preferably on a different skin site. For example, for a 7-day device, maintenance would involve replacing the device every 7 days with a fresh device and continuing said replacement for as long as contraception was desired. In one method of obtaining effective contraception, it may be desired to apply devices containing gestodene and estrogen for a period of three weeks, followed by application for one week of a device as disclosed herein but containing only the estrogen.

Thus, another embodiment of this invention is directed to a kit for a 28-day contraceptive cycle. The kit would include four 7-day transdermal devices. Three of the devices would codeliver gestodene and estrogen and one device would deliver only estrogen or alternatively would be a placebo. The three gestodene/estrogen patches would deliver about a constant amount of estrogen, but each device would deliver a varying amount of gestodene based upon the hormonal requirement of the woman during her menstrual cycle.

The transdermal therapeutic devices of the present invention are prepared in a manner known in the art, such as by those procedures, for example, described in the transdermal device patents listed previously herein.

For each device tested, the release liner was removed and the drug-releasing surface was placed against the stratum corneum side of a disc of epidermis which had been blotted dry just prior to use. The excess epidermis was wrapped around the device so that none of the device edge was exposed to the receptor solution. The device covered with epidermis was attached to the flat side of the Teflon holder of a release rate rod using nylon netting and nickel wire. The rods were reciprocated in a fixed volume of receptor solution (distilled water). The entire receptor solution was changed at each sampling time. The temperature of the receptor solution in the water bath was maintained at 35° C.

A summary of the results is given in Table 1 below.

TABLE 1

| | 3.5 cm² System | | | | | |
|---|---|---|---|---|---|---|
| Skin Donor | Experimental GTD mcg/day | Experimental $EE_2$ mcg/day | Theoretical GTD mcg/day | Theoretical $EE_2$ mcg/day | Ratio GTD/$EE_2$ Theoretical | Ratio GTD/$EE_2$ Experimental |
| 1 | 19.3 | 35.6 | 25 | 50 | 0.50 | 0.54 |
| 2 | 21.7 | 41.7 | 25 | 50 | 0.50 | 0.52 |
| 3 | 18.6 | 36.6 | 25 | 50 | 0.50 | 0.51 |

The following examples are offered to illustrate the practice of the present invention and are not intended to limit the invention in any manner.

EXAMPLE 1

The drug/permeation enhancer reservoir was prepared by mixing ethylene vinyl acetate having a vinyl acetate content of 40 percent ("EVA 40", U.S.I. Chemicals, Illinois)in an internal mixer (Bra Bender type mixer) until the EVA 40 fellets fused. Gestodene, ethinyl estradiol and glycerol monooleate (Myverol® 1899K, (Eastman Chemical Products) were then added. The mixture was blended for approximately 20 minutes at 54°–56° C. and 30 rpm. After blending, the mixture was quickly cooled to 40°–45° C. and calendared to a 5 mils thick film. The film was then laminated to a NRU-100-C backing on one side and a 3M acrylate transfer adhesive MSP 32589 on the other. The film was then cut into circles using a stainless steel punch. The final composition of the drug/permeation enhancer reservoir The in vitro cumulative amount transported through the epidermis for gestodene and ethinyl estradiol from a 3.5 cm² system were determined and compared against the theoretical ratios determined for the same size system.

EXAMPLE 2

The in vitro cumulative amount transported through epidermis for gestodene and ethinyl estradiol from a 7 cm² system were determined and then compared against the theoretical ratios determined for the same system following the procedures of Example 1. The final drug/permeation enhancer reservoir composition (weight percent) was as follows: 4.2% $EE_2$.; 4.0% GTD; 30% GMO and 61.8% EVA 40. A summary of the results is given in Table 2 below.

TABLE 2

| | 7.0 cm² System | | | | | |
|---|---|---|---|---|---|---|
| Skin Donor | Experimental GTD mcg/day | Experimental $EE_2$ mcg/day | Theoretical GTD mcg/day | Theoretical $EE_2$ mcg/day | Theoretical Ratio GTD/$EE_2$ | Experimental Ratio GTD/$EE_2$ |
| 1 | 41.0 | 38.9 | 50 | 50 | 1.00 | 1.06 |
| 2 | 66.3 | 62.1 | 50 | 50 | 1.00 | 1.07 |
| 3 | 46.1 | 45.3 | 50 | 50 | 1.00 | 1.02 | composition (weight percent) was as follows 8.5% $EE_2$; 4.0% GTD; 30% GMO; and 57.5% EVA 40.

The edges of the device were masked with polyester tape so that the drug reservoir was not exposed to the epidermis or solutions when they were tested.

The epidermis was separated from the dermis of the skin donor after immersion in 60° C. water for 75 seconds. Discs (⅞-inch diameter) were cut from the epidermis, and the discs were kept at 4° C. in a hydrated state until they were used.

EXAMPLE 3

The in vitro cumulative amount transported through epidermis for gestodene and ethinyl estradiol from a 14.0 cm² system were determined and compared against the theoretical ratios determined for the same size system following the procedures of Examples 1 and 2. The final drug/permeation enhancer reservoir (weight percent) was as follows: 2.1% $EE_2$; 4.0% GTD; 30% GMO; and 63.9% EVA 40. A summary of the results is given in Table 3 below.

TABLE 3

| | 14.0 cm² System | | | | | |
|---|---|---|---|---|---|---|
| Skin Donor | Experimental GTD mcg/day | Experimental $EE_2$ mcg/day | Theoretical GTD mcg/day | Theoretical $EE_2$ mcg/day | Theoretical Ratio GTD/$EE_2$ | Experimental Ratio GTD/$EE_2$ |
| 1 | 52.7 | 28.9 | 100 | 50 | 2.0 | 1.83 |
| 2 | 118.6 | 58.9 | 100 | 50 | 2.0 | 2.01 |
| 3 | 108.3 | 54.3 | 100 | 50 | 2.0 | 1.99 |

Figure 4:
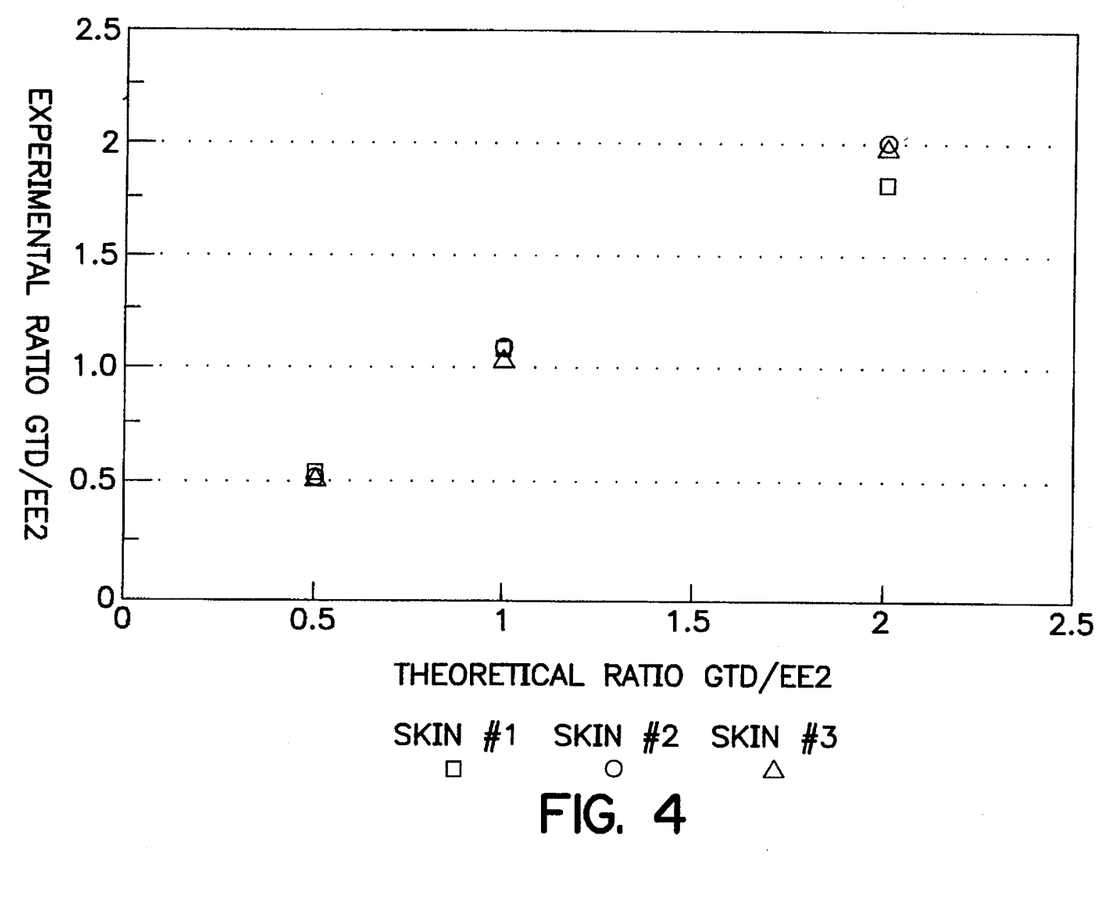
FIG. 4 is a graph showing a plot of the in vitro cumulative amount of drug transported across epiderms ratios of gestodene to ethinyl estradiol for various system sizes versus the theoretical ratios observed using transdermal delivery devices of this invention.

A plot of the experiment ratios versus the theoretical for each of the examples is depicted in FIG. 4. As is shown in FIG. 4, the slope of the graph is approximately 1, thus indicating that the experimental ratios correspond to the theoretical ratios. Therefore, the systems were properly formulated to codeliver a constant amount of estrogen from various sizes of systems while the amount of gestodene codelivered varied as the system size increased.

This invention has been described in detail with particular reference to certain preferred embodiments thereof, but it will be understood that variations and modifications can be effected within the spirit and scope of the invention.

What is claimed is:

1. A method for the transdermal coadministration of an estrogen and gestodene through the skin from a drug formulation comprised of ethinyl estradiol and gestodene, which method comprises:
   (a) placing a transdermal delivery device on the skin of a person, the device comprising:
      (i) a reservoir comprising ethinyl estradiol, gestodene and a monoglyceride skin permeation enhancer,
      (ii) a backing on the skin-distal surface of the reservoir, and
      (iii) means for maintaining the reservoir in ethinyl estradiol-gestodene-and monoglyceride-transmitting relation with the skin,
   whereby ethinyl estradiol and gestodene are coadministered through an area of skin at contraceptively effective rates, and said monoglyceride permeation enhancer is simultaneously coadministered to the area of skin at rates which are sufficient to substantially increase the permeability of the area to at least one of said ethinyl estradiol and gestodene.

2. A method according to claim 1 wherein the administration rate of ethinyl estradiol is maintained at a substantially constant rate of about 30–50 µg/day for a predetermined period of time while the administration rate of gestodene is varied between a first level of about 25 µg/day for a predetermined period of time, a second level of about 100 µg/day for a predetermined period of time, and a third level of about 50 µg/day for a predetermined period of time.

3. A method according to claim 2 wherein the administration rate of gestodene is increased by increasing the base surface area of the transdermal drug delivery device.

4. A method for providing contraception to a woman comprising:
   (a) placing a transdermal delivery device on an area of the woman's skin, the device comprising:
      (i) a reservoir comprising ethinyl estradiol, gestodene and a monoglyceride skin permeation enhancer,
      (ii) a backing on the skin-distal surface of the reservoir, and
      (iii) means for maintaining the reservoir in ethinyl estradiol-gestodene-and monoglyceride-transmitting relation with the skin,
   whereby ethinyl estradiol and gestodene are coadministered through the area of skin at contraceptively effective, but not necessarily equal rates, and said monoglyceride permeation enhancer is simultaneously coadministered to the area of skin at rates which are sufficient to substantially increase the permeability of the area to at least one of said ethinyl estradiol and gestodene.

5. A method according to claim 4 wherein the administration rate of ethinyl estradiol is maintained at a substantially constant rate of about 30–50 µg/day for a predetermined period of time while the administration rate of gestodene is varied between a first level of about 25 µg/day for a predetermined period of time, a second level of about 100 µg/day for a predetermined period of time, and a third level of about 50 µg/day for a predetermined period of time.

6. A method according to claim 5 wherein the administration rate of gestodene is increased by increasing the base surface area of the transdermal drug delivery device.

7. A method according to claim 1 wherein the permeation enhancer is glycerol monooleate, glycerol monolinoleate or glycerol monolaurate.

8. A method according to claim 1 wherein the permeation enhancer is glycerol monooleate.

9. A method according to claim 8 wherein the ethinyl estradiol and gestodene are administered through the skin at equal rates.

10. A method according to claim 8 wherein the ethinyl estradiol and gestodene are administered through the skin at unequal rates.

11. A method according to claim 7 wherein the gestodene and ethinyl estradiol are administered through the skin at a rate of from about 30 µg/day to about 50 µg/day for a predetermined period of time.

12. A method according to claim 10 wherein the ethinyl estradiol is administered through the skin at a rate from about 30 µg/day to about 50 µg/day for a predetermined period of time and the gestodene is administered through the skin at a rate of about 100 µg/day for a predetermined period of time.

13. A method according to claim 10 wherein the ethinyl estradiol is administered through the skin at a rate from about 30 µg/day to about 50 µg/day for a predetermined period of time and the gestodene is administered through the skin at a rate of about 25 µg/day for a predetermined period of time.

14. A method according to claim 4, wherein the permeation enhancer is glycerol monooleate, glycerol monolinoleate or glycerol monolaurate.

15. A method according to claim 4 wherein the permeation enhancer is glycerol monooleate.

16. A method according to claim 14, wherein the ethinyl estradiol and gestodene are administered through the skin at equal rates.

17. A method according to claim 14 wherein the ethinyl estradiol and gestodene are administered through the skin at unequal rates.

18. A method according to claim 14, wherein the ethinyl estradiol and gestodene are administered through the skin at a rate from about 30 µg/day to about 50 µg/day for a predetermined period of time.

19. A method according to claim 17, wherein the ethinyl estradiol is administered through the skin at a rate from about 30 µg/day to about 50 µg/day for a predetermined period of time and the gestodene is administered through the skin at a rate of about 100 µg/day for a predetermined period of time.

20. A method according to claim 17, wherein the ethinyl estradiol is administered through the skin at a rate from about 30 µg/day to about 50 µg/day for a predetermined period of time and the gestodene is administered through the skin at a rate of about 25 µg/day for a predetermined period of time.

21. A device for the transdermal coadministration of an estrogen and gestodene, at a contraceptively effective, but not necessarily equal rate, from a drug formulation comprised of ethinyl estradiol and gestodene, which device comprises:

(a) a reservoir comprising a matrix containing an amount of each of the components of the drug formulation such that each component is delivered at a contraceptively effective, but not necessarily equal rate, and a skin permeation-enhancing amount of a monoglyceride permeation enhancer;

(b) a backing on the skin-distal surface of the reservoir; and (c) means for maintaining the reservoir in ethinyl estradiol-gestodene-and monoglyceride-transmitting relation with the skin.

22. A device according to claim 21, wherein the permeation enhancer is glycerol monooleate, glycerol monolinoleate or glycerol monolaurate.

23. A device according to claim 21 wherein the permeation enhancer is glycerol monooleate.

24. The device of claim 22 wherein the ethinyl estradiol and gestodene are administered through the skin at equal rates.

25. The device of claim 22 wherein the ethinyl estradiol and gestodene are administered through the skin at unequal rates.

26. A device according to claim 25, wherein the estradiol is administered through the skin at a rate from about 30 µg/day to about 50 µg/day for a predetermined period of time and the gestodene is administered through the skin at a rate of about 25 µg/day for a predetermined period of time.

27. A method according to claim 22, wherein the ethinyl estradiol is administered through the skin at a rate from about 30 µg/day to about 50 µg/day for a predetermined period of time and the gestodene is administered through the skin at a rate of about 50 µg/day for a predetermined period of time.

28. A method according to claim 25, wherein the ethinyl estradiol is administered through the skin at a rate from about 30 µg/day to about 50 µg/day for a predetermined period of time and the gestodene is administered through the skin at a rate of about 100 µg/day for a predetermined period of time.

29. A device according to claim 26 having a base surface area about 3.5 cm$^2$ in size.

30. A device according to claim 27 having a base surface area about 7.0 cm$^2$ in size.

31. A device according to claim 28 having a base surface area about 14.0 cm$^2$ in size.

* * * * *